United States Patent
Linares

(10) Patent No.: US 8,257,290 B2
(45) Date of Patent: Sep. 4, 2012

(54) TEMPORARY SPLINT ASSEMBLY WITH SEMI-RIGID WRAP AROUND SUPPORTS IN COMBINATION WITH INTERMEDIATELY POSITIONED JOINT CAST

(75) Inventor: Miguel A. Linares, Bloomfield Hills, MI (US)

(73) Assignee: Linares Medical Devices, LLC, Auburn Hills, MI (US)

(*) Notice: Subject to any disclaimer, the term of this patent is extended or adjusted under 35 U.S.C. 154(b) by 441 days.

(21) Appl. No.: 12/554,179

(22) Filed: Sep. 4, 2009

(65) Prior Publication Data
US 2010/0063433 A1  Mar. 11, 2010

Related U.S. Application Data

(60) Provisional application No. 61/094,438, filed on Sep. 5, 2008.

(51) Int. Cl.
*A61F 5/00* (2006.01)
(52) U.S. Cl. .............. 602/12; 602/20; 602/23; 602/26
(58) Field of Classification Search .......... 602/5, 6, 602/12, 14, 16, 20, 23, 26; 128/846, 878, 128/881, 882; 2/22, 24, 239, 240, 241, 242
See application file for complete search history.

(56) References Cited

U.S. PATENT DOCUMENTS

| | | | |
|---|---|---|---|
| RE27,957 E * | 4/1974 | Larson | 602/12 |
| 3,955,565 A * | 5/1976 | Johnson, Jr. | 602/12 |
| 4,111,194 A | 9/1978 | Cox et al. | |
| 4,727,865 A * | 3/1988 | Hill-Byrne | 602/6 |
| 5,306,230 A | 4/1994 | Bodine | |
| 5,387,185 A | 2/1995 | Johnson, Jr. et al. | |
| 5,836,902 A * | 11/1998 | Gray | 602/5 |
| 6,000,402 A | 12/1999 | Able | |
| 6,942,629 B2 | 9/2005 | Hepburn et al. | |
| 7,513,881 B1 | 4/2009 | Grim et al. | |
| 7,704,218 B2 * | 4/2010 | Einarsson et al. | 602/16 |
| 7,713,225 B2 * | 5/2010 | Ingimundarson et al. | 602/26 |
| 7,762,973 B2 * | 7/2010 | Einarsson et al. | 602/26 |
| 2005/0065458 A1 | 3/2005 | Kim | |
| 2005/0080369 A1 | 4/2005 | Kim | |
| 2006/0135904 A1 * | 6/2006 | Ingimundarson et al. | 602/26 |
| 2007/0083136 A1 * | 4/2007 | Einarsson | 602/26 |
| 2008/0065230 A1 | 3/2008 | Nordt et al. | |
| 2008/0154164 A1 | 6/2008 | Sheehan et al. | |
| 2008/0195013 A1 | 8/2008 | Ingimundarson et al. | |
| 2009/0188445 A1 | 7/2009 | Jacobsen | |

FOREIGN PATENT DOCUMENTS

IE   20050593 A1   3/2006
JP   2000005247 A   1/2000

* cited by examiner

*Primary Examiner* — Patricia Bianco
*Assistant Examiner* — Raymond E Harris
(74) *Attorney, Agent, or Firm* — Gifford, Krass, Sprinkle, Anderson & Citowski, P.C.

(57) ABSTRACT

A splint assembly for use with an individual's limb including an assembleable and rigid member positioned in surrounding fashion about an intermediate joint associated with the limb. A pair of support subassemblies secure about a location of the individual's limb contiguous to the joint, an extending edge of each support subassembly securing to a perimeter extending edge of the rigid member. Upper and lower wraparound support subassemblies secure to first and second perimeter extending edges associated with the rigid member, each further including a generally grid and web-shaped foam template with a hardened plastic backing being configured to match the configuration of the foam template. Edge extending straps provided for each of the hardened plastic backings overlap and engage opposite extending edge locations of each wraparound support subassembly.

10 Claims, 4 Drawing Sheets

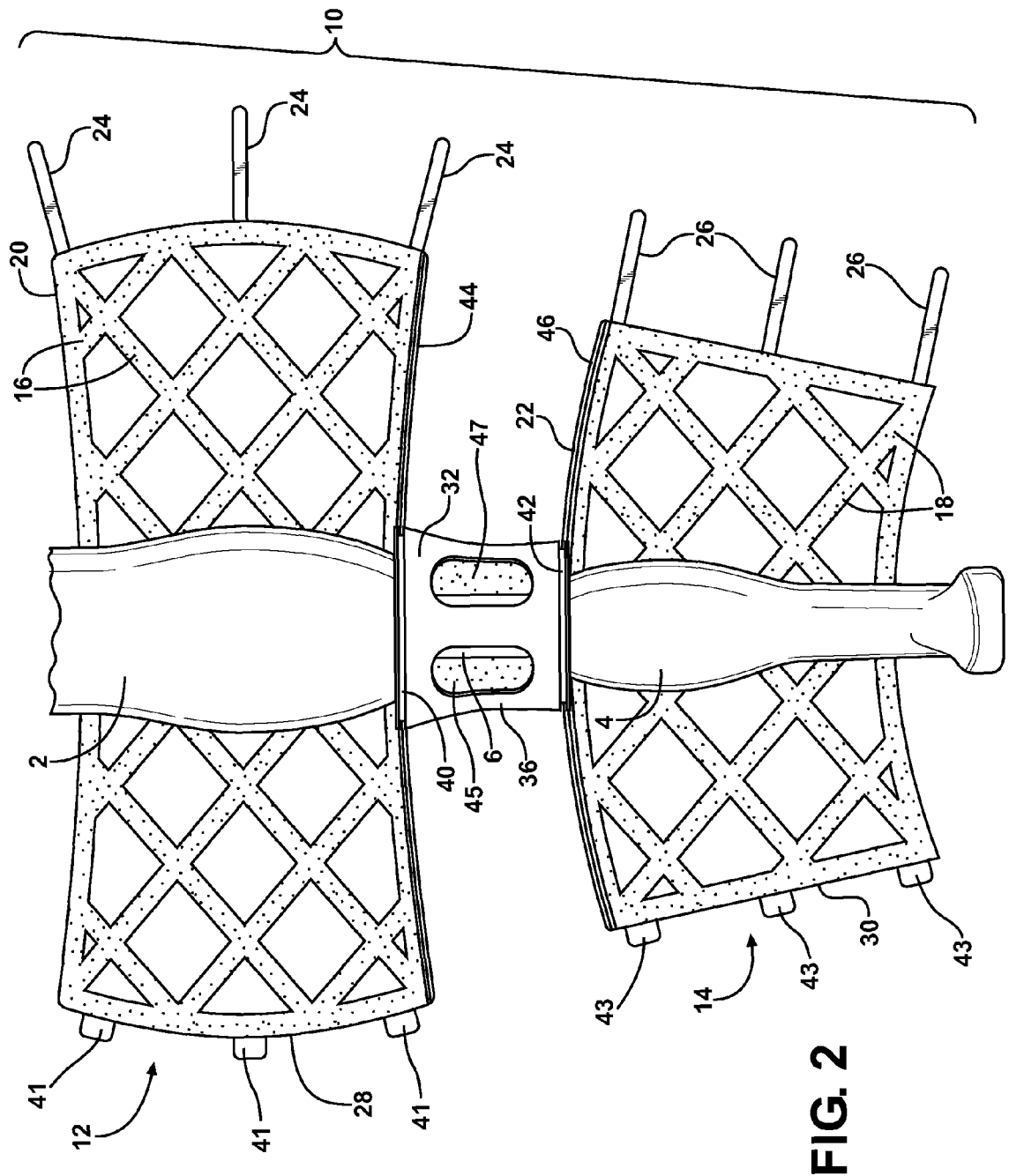

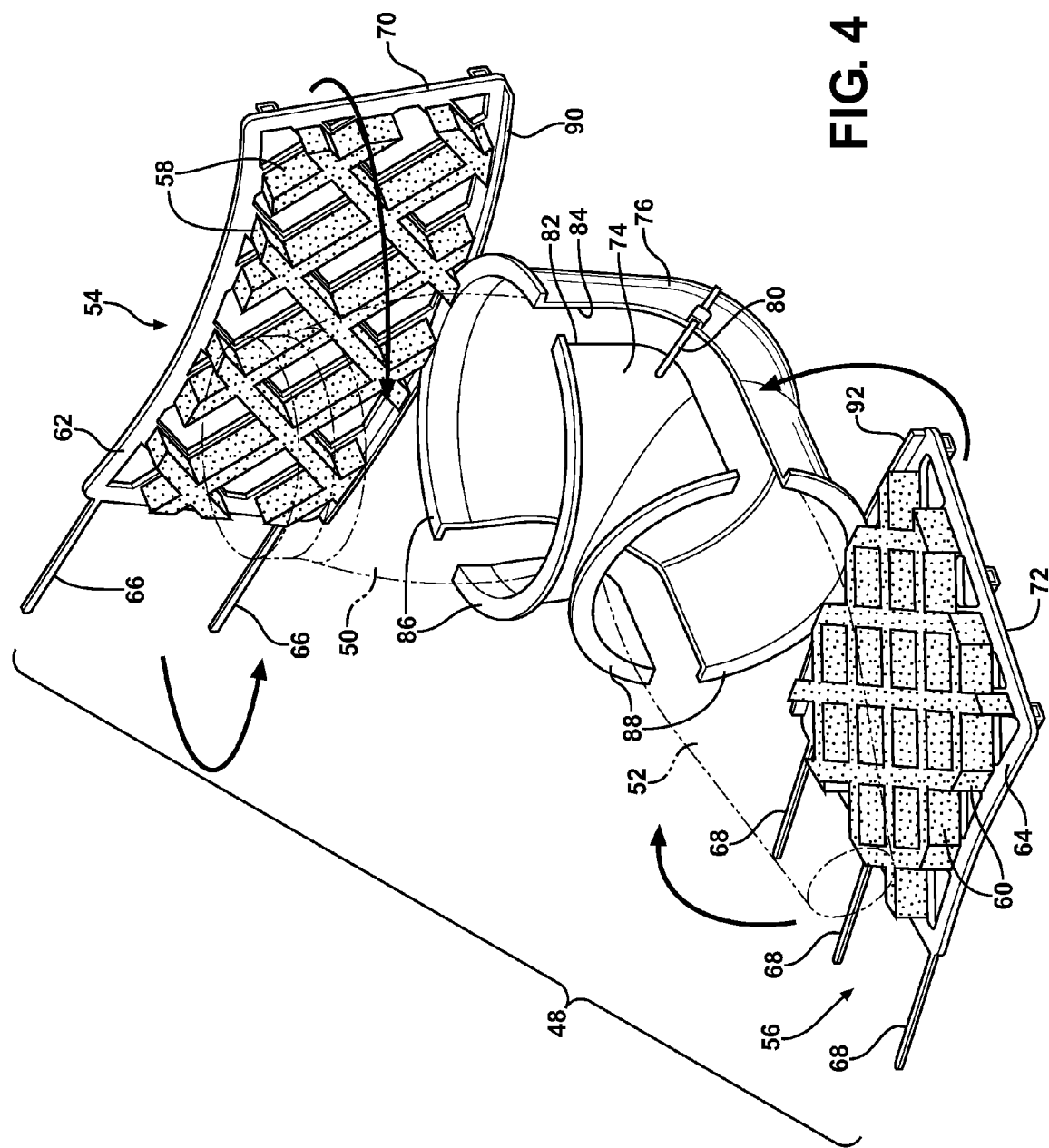

TEMPORARY SPLINT ASSEMBLY WITH SEMI-RIGID WRAP AROUND SUPPORTS IN COMBINATION WITH INTERMEDIATELY POSITIONED JOINT CAST

CROSS REFERENCE TO RELATED APPLICATIONS

The present application claims priority of U.S. Provisional Patent Application Ser. No. 61/094,438 filed Sep. 5, 2008.

FIELD OF THE INVENTION

The present invention relates generally to a temporary splint assembly for immobilizing a user's limb, such as in response to a bone sprain, dislocation or fracture. More specifically, the present invention discloses a temporary splint assembly incorporating upper and lower semi-flexible web portions, such as corresponding to upper/lower leg or arm locations, the web portions engaging opposite extending edges of a knee/elbow joint located and supported collar. The splint assembly is advantageously used by first responders or other emergence medical personal, for the purpose of immobilizing a wounded limb, and until such time as appropriate professional medical personnel can substitute the splint with a limb cast or the like.

DESCRIPTION OF THE PRIOR ART

The prior art is documented with examples of cast assemblies, these including both temporary and permanent casts for providing an acceptable degree of immobilizing support to an injured limb associated with the wearer. Examples of known commercial variants of cast include the provision of either a rigid pre-formed or settable material which is configured about a user's injured limb, typically following resetting or realigning a sprain, break or fracture, and which hardens to provide immobilizing support to the user for the period of time necessary to adequately heal the break. Disadvantages associated with such rigid applied casts include the relative lack of ventilation accessible to the user's skin in addition to their relative bulkiness in use.

SUMMARY OF THE PRESENT INVENTION

The present invention discloses a splint assembly for use, such as by emergency medical first responding technicians, with an individual's limb including a leg or arm, and which includes a generally two-piece assemblable rigid member positioned in surrounding fashion about an intermediate joint associated with the limb. At least one, and typically a pair, of semi-rigid/semi-flexible support subassemblies secure about locations of the individual's limb contiguous to and in connecting fashion with the rigid joint, an extending edge of each support subassembly securing to a perimeter extending edge of assembled rigid member.

The support subassemblies each further include upper and lower wraparound support subassemblies for securing to the first and second perimeter extending edges associated with the rigid member. The wraparound support subassemblies are each provided as generally grid and web-shaped foam templates, over which is configured a hardened plastic backing. Edge extending straps are provided for each of the hardened plastic backings, the pluralities of straps overlapping and engaged opposite extending edge locations of each wraparound support subassembly. In use, the support members are each assembled so as to define oppositely extending perimeter edges, each of which exhibits a first seating profile which is engaged by an opposing extending edge of the support subassembly.

Additional features associated with the assembleable rigid members include, depending upon the variant, providing the assembleable members in generally semi-cylindrical shaped members, such as corresponding to a knee cast, or shaping the assembleable members as a pair of elbow shaped members in the further instance of an arm cast. At least one clamp is provided for securing and drawing together the elbow shaped members according to the arm cast variant. The rigid assembleable members each are further constructed of a durable material including at least a lightweight metal or a rigid and impact resistant plastic/composite polymer composition and further exhibit one or more interiorly defined apertures in order to provide a desired degree of ventilation to the individuals kneecap.

BRIEF DESCRIPTION OF THE DRAWINGS

Reference will now be made to the attached drawings, when read in combination with the following detailed description, wherein like reference numerals refer to like parts throughout the several views, and in which:

FIG. 2 is a rotated front view of the illustration shown in FIG. 1;

FIG. 4 is an illustration similar to FIG. 1 of a further modified variant of temporary splint support configured for engaging and immobilizing a patient's arm.

DETAILED DESCRIPTION OF THE PREFERRED EMBODIMENTS

As previously described, the present invention discloses a temporary splint assembly incorporating upper and lower semi-rigid and semi-flexible web portions, such as corresponding to upper/lower leg or arm locations. As will be further described and illustrated throughout reference to FIGS. 1-5, the web portions are wrapped around upper/lower limb locations associated with either a wearer's leg (FIGS. 1-3) or arm (FIGS. 4 and 5) and in order to engage opposite extending edges of an associated knee/elbow rigid assembleable joint locating and supported collar. The splint assembly is advantageously used by first responders or other emergence medical personal, for the purpose of immobilizing a wounded limb, and until such time as appropriate professional medical personnel can substitute the splint with a more permanent limb cast or the like.

Figure 3:
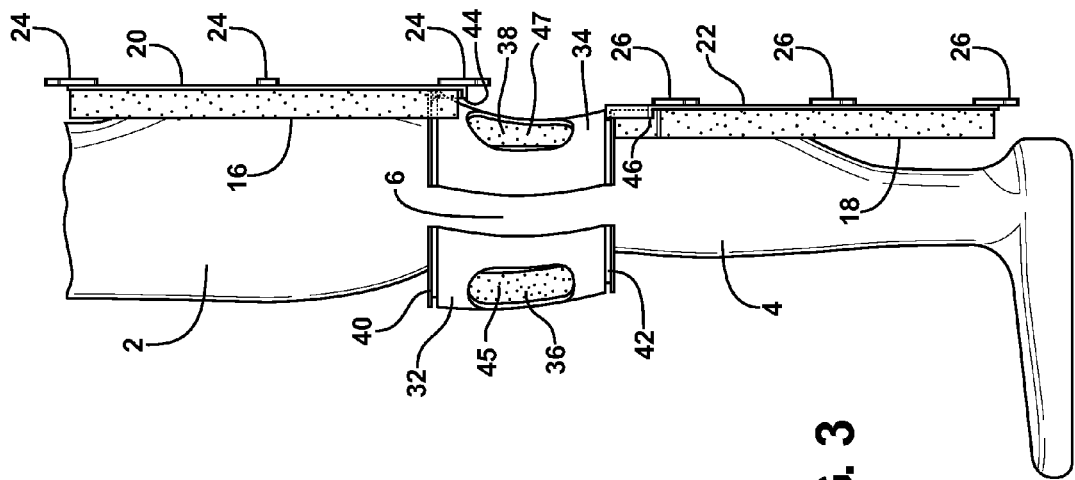
FIG. 3 is a further rotated side view and further showing the two piece assembleable nature of the joint supported rigid collar.
Figure 1:
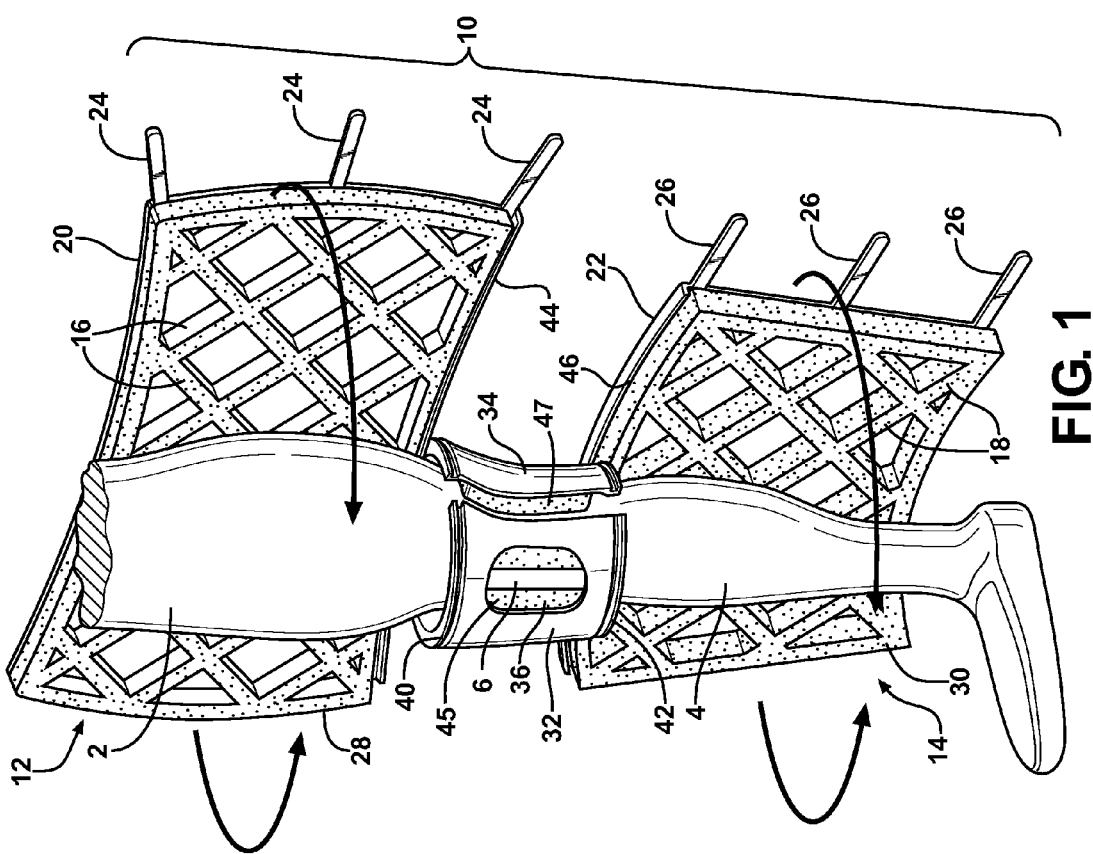
FIG. 1 is a partially assembled environmental perspective illustration of a first variant of immobilizing leg splint and including first/upper and second/lower wraparound splint supports, each engageable with an opposite extending edge boundary associated with an intermediately positioned and assembled rigid collar, such as supported over a knee joint.

Referring to each of FIGS. 1-3, a series of partially assembled environmental perspective and front/side illustrations are shown of a first variant of immobilizing splint assembly 10 for engagement over a individual's leg, and which as is known includes an upper leg (including femur) 2, lower leg (including tibia and fibula) 4 and intermediately located knee joint (with patella) 6. As will also be further disclosed in reference to FIGS. 4 and 5, the temporary splint assembly can also be modified for application to such as an injured arm.

An upper wraparound support subassembly is generally shown at 12 and a corresponding lower wraparound support subassembly is further generally shown at 14. Each of the wraparound supports includes a generally grid and web-shaped foam template, see respectively at 16 and 18 for upper 12 and lower 14 supports. A hardened plastic backing, at 20 and 22, is further provided for each wraparound support, each of the backings being configured to match the configuration of the foam templates 16 and 18 and such that the foam templates are glued or otherwise adhesively secured in aligning fashion with the hardened plastic backings. Additional variants can contemplate integrating the foam applying (grid) layers and associated hardened plastic backing layers into a single composite and unitary material, and such as which may exhibit both the desired properties of flexibility and enduring rigidity in application.

Edge extending straps, see as shown at 24 and 26, respectively are provided for each of the hardened plastic backings 20 and 22 associated with the upper wraparound support 12 and lower wraparound support 14. The individual pluralities of straps 24 and 26 are provided for overlapping and engaged opposite extending edge locations (see at 28 and 30, respectively) of the wraparound support subassemblies 12 and 14.

The support subassemblies 12 and 14 are intended to exhibit a modified mixture of flexibility and rigidity, such as in order to be applied about a user's limb, while at the same time exhibiting a necessary degree of rigidity to protect the limb after being applied. Accordingly, and in the embodiment illustrated, the web/grid shaped templates 16 and 18 each are constructed of a spongy foam-like material, such as which is again adhered by adhesives or the like to a surface of the more rigid/hardened plasticized hardened backings, again 20 and 22. The generally web (honeycomb) configuration of the foam templates and plastic backing layers is further intended to provide a desired amount of material, exhibiting a suitable flexibility, and while at the same time providing an optimal degree of ventilation to the limb.

A joint located rigid support member is disposed upon the individual's limb, such as over the knee joint as disclosed in FIGS. 1-3, and includes, in the illustrated embodiment, a pair of first 32 and second 34 generally semi-cylindrical shaped rigid and assembleable members. Each of the members 32 and 34 is constructed of a durable material, such as a lightweight metal or a rigid and impact resistant plastic/composite polymer composition, and each may further include one or more interiorly defined apertures, see further shown as respective pairs of interior apertures as evidenced by interior extending and boundary defining surfaces 36 and 38, this in order to provide a desired degree of ventilation to the individuals kneecap 6. In addition to the rigid support member being assembled as two individual pieces, such as further including the provision of opposing edge extending slot and tab or other snap fit structure, it is also envisioned that the members 32 and 34 can be clam-shell connected together or otherwise provided a one piece subassembly defining a common hinged connection, this facilitating assembly about the user's knee joint 6.

As illustrated in each of FIGS. 1-3, the members 32 and 34 define oppositely extending upper 40 and lower 42 perimeter edges. The perimeter edges 40 and 42 each exhibit a slightly inwardly stepped recessed configuration this defining a seating channel located proximate the upper and lower edges of the rigid member, and which is engaged by an associated bottom most extending edge 44 of the upper backing 20 as well as an upper most extending edge 46 of the lower backing 22. Reference in particular is made to each of the illustrations of FIGS. 1-3, in particular the frontal view of FIG. 2, and which illustrates the pre-aligning of the edges 44 and 46 relative to the upper 40 and lower 42 seating channels defined by the members 32 and 34, as well as the perspective view of FIG. 1 in which the inwardly projecting and aligning edges 44 and 46 of the backing members 20 and 22 align in overlapping and channel seating fashion with the recessed perimeter edges 40 and 42 extending around opposite ends of the members 32 and 34.

Upon wrapping the semi-rigid (semi-flexible) support subassemblies 12 and 14 about the user's upper 2 and lower 4 limb portions (see associated directional arrows in FIG. 1), the overlapping portions of the respective straps 24 and 26 are then fastened to the opposite and aligning edge of the rigid backing layers. In this fashion, the associated edges 44 and 46 of the backings 20 and 22 are progressively seated within the perimeter defined channels associated with the edges 44 and 46 of the members 32 and 34, thus securing each semi-flexible support subassembly to the rigid intermediate assembled support member in such a fashion as to create a unitary splint assembly.

For purposes of clarity of illustration, the illustrations of FIGS. 1-3 illustrate the support subassemblies 12 and 14 in pre-positioned and unfolded fashion relative to the partially assembled (partially exploded) members 32 and 34, it being understood that the extending straps 24 and 26 engage suitable surface defined locations (hidden from view) associated with the back surface of the rigid backing layers 20 and 22 to secure the support subassemblies in conforming fashion about the user's limb. It is also envisioned that the engagement interface established between the straps 24 and 26 and the receiving back surfaces of the backings 20 and 22 (see FIG. 3) can include some degree of adjustability. This can include the opposite/aligning edges of the backings 20 and 22 including a buckle, tab or other suitable engagement structure as is shown by pluralities of inter-engagement structure shown at 41 and 43 in the front plan view of FIG. 2. Although not shown, it is understood that the engagement tabs or the like can include clamping or pinching like structure or can include a buckle interfacing with selected apertures (not shown) defined in the straps 24 and 26.

In this fashion, the inwardly facing and sponge-like support grids 16 and 18, associated with the support subassemblies 12 and 14, collectively provide, along with the intermediate joint located rigid support, a temporary, quickly applied and effective splint for immobilizing a user's limb, this prior to the individual receiving appropriate medical attention (further including such as re-setting a bone fracture and/or applying a permanent cast). Depending further upon the material properties of the support subassemblies, and in particular a degree of stretch which also may be associated with its semi-flexible design, a minimal number of differently sized subassemblies can be provided for engaging different sized limbs. The inner facing surfaces of the assembled rigid members 32 and 34 can also include foam inserts 45 and 47, such capable of being interchangeable in order to adjust to varying dimensions associated with the wearer's limb.

Figure 5:
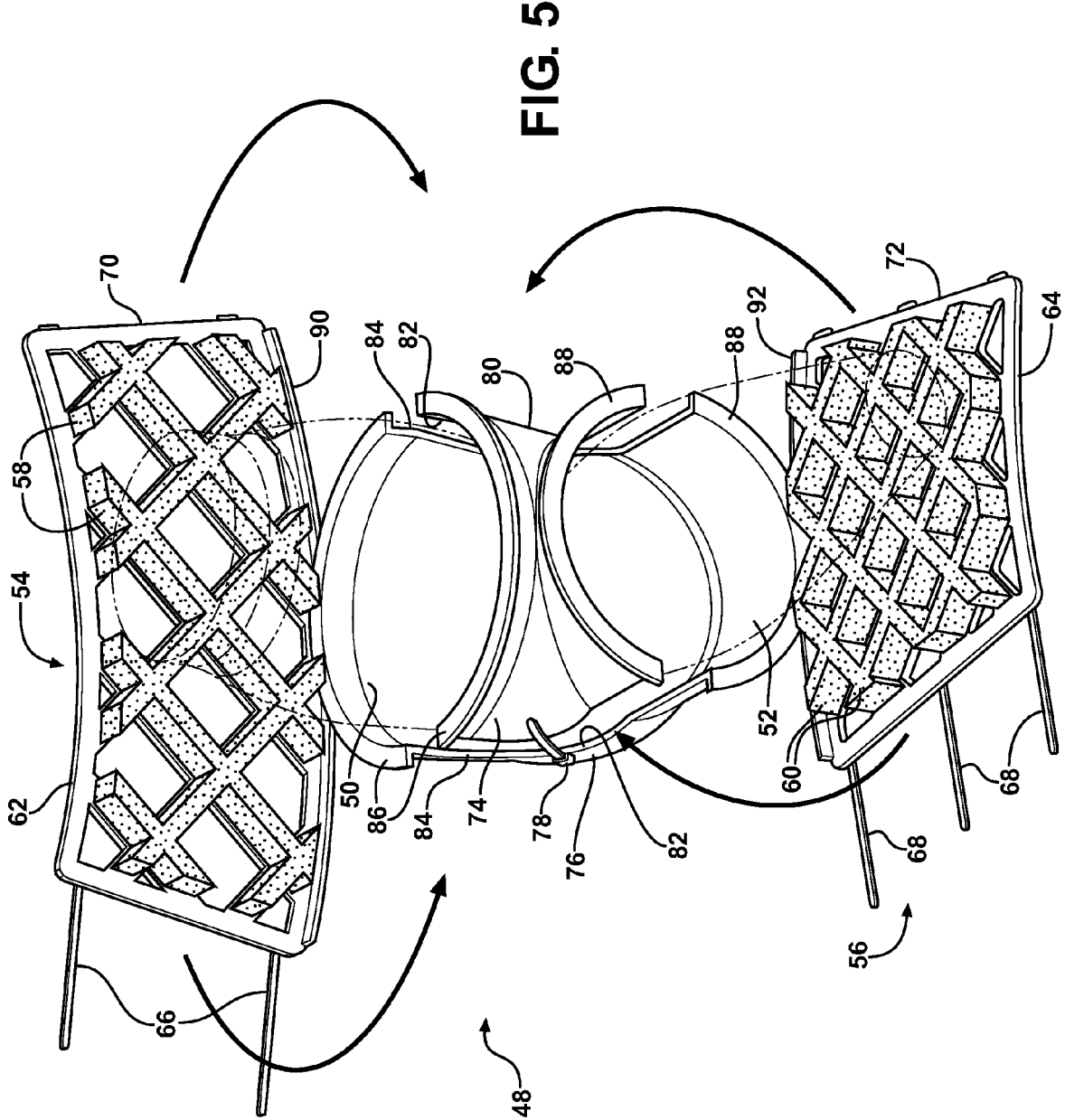
FIG. 5 is a rotated and generally front perspective view of the illustration shown in FIG. 4.

Referring now to FIGS. 4 and 5, a pair of illustrations are shown, similar to FIG. 1, of a further modified variant 48 of a temporary splint support configured for engaging and immobilizing a patient's arm and which includes an upper arm 50 (including humerus bone) and an interconnecting lower arm 52 (including ulna and radius bones). The variant 48 operates along the same principle as for that shown at 10 in reference to the leg splint assembly and includes both an upper wraparound support subassembly 54 and a corresponding lower wraparound support subassembly 56.

Each of the wraparound supports again includes a generally grid and web-shaped foam template, see respectively at 58 for upper support subassembly 54 and at 60 for lower support subassembly 56. Hardened plastic backings, at 62 and 64, are further provided for each wraparound support, each of the backings again being configured to match the configuration of the matingly aligned and secured foam templates 58 and 60 and to which the foam and cushioning templates are adhesively or otherwise secured.

Individual pluralities of edge extending straps are again shown at 66 and 68, respectively, and are provided for each of the hardened plastic backings 62 and 64, again associated with the upper wraparound support 54 and lower wraparound support 56. The pluralities of straps 66 and 68 are provided for overlapping and engaged opposite extending edge locations (see at 70 and 72) of the wraparound support subassemblies 54 and 56 in a similar fashion as described with reference to the variant of FIGS. 1-3, and is also understood to include the provision of some form of inter-engaging or fastening structure associated with the opposite and folded/aligning edge of each wrap around subassembly (this as previously represented at 41 and 43 in FIG. 2).

As with the first variant, 10, the support subassemblies 54 and 56 are intended to exhibit a modified mixture of flexibility and rigidity, such as in order to be applied about a user's (arm) limb, while at the same time exhibiting a necessary degree of rigidity to protect the limb after being applied. Accordingly, and in the embodiment illustrated, the web/grid shaped templates 58 and 60 are each again constructed of a spongy foam-like material, such as which is adhered by adhesives or the like to a surface of the more rigid/hardened plasticized backings 62 and 64. As was described previously in reference to the leg split wraparound supports, the generally web (honeycomb) configuration of the foam templates and plastic backing layers is further intended to provide a desired amount of material, exhibiting suitable characteristics of both flexibility in application as well as rigidity in use, and while at the same time providing an optimal degree of ventilation to the limb.

A joint located rigid support member is disposed upon the individual's limb, such as over the elbow joint and, according to this variant, includes a pair of first (upper and forward positioned) rigid elbow shaped member 74 and second (lower and rearward positioned) 76 rigid elbow shaped nesting member. Each of the members 74 and 76 is constructed of a durable material, such as a lightweight metal or a rigid and impact resistant plastic/composite polymer composition, and each further defines a substantially semi-circular shape in either angled cross sectional profile.

The upper/forward elbow shaped member 74 is dimensioned to be somewhat smaller than the lower/rearward elbow shaped member 76 such that, upon positioning over the individual's aim as referenced by the angular position exhibited by the arm portions 50 and 52, the rigid members 74 and 76 can be secured together. This is accomplished by the provision of one or more clamps, see at 78 and 80, extending between adjoining and opposing profile surfaces, see further at 82 and 84 along each of first and second sides established between the assembled elbow shaped members 74 and 76. An appropriate tool (not shown) is employed for tightening/loosening the clamps 78 and 80 and it is also envisioned that other clamp assemblies can be employed within the scope of the invention.

The clamps 78 and 80 secure to selected side locations of the overlapping elbow members 74 and 76 and, upon being tightened a desired degree, draw the elbow shaped members 74 and 76 together to immobilize the individual's arm about the elbow joint region established therebetween. Although not shown, the elbow shaped and aligning members can include internal positioned foam inserts (such as shown at 45 and 47 in FIGS. 1-3). As was also described in reference to the variant 10 of FIGS. 1-3, other structure is also contemplated for securing together the elbow members, this including such as tab and slot fasteners, hinged structures, as well as the provision of length adjustable straps (e.g. modified zip strip structures) for loosely engaging the joint defining members in a first pre-positioning step, following which the straps/zip strips are drawn down (or tightened) in order to align their opposing edges (see again at 82 and 84) and to immobilize the individual's arm at the location of the elbow joint.

As with the knee joint assembly 10, the assembled elbow joint support members 74 and 76 collectively define oppositely and angularly extending upper 86 and lower 88 perimeter edges. The perimeter edges 86 and 88 according to the elbow variant each exhibit an outwardly angled ledge configuration, these being engaged by inwardly angled ledges 90 and 92 extending from inner most opposing and extending edges of each of the upper support member rigid backing 62 as well as an upper most extending edge of the lower support member rigid backing 64.

Upon wrapping the semi-rigid (semi-flexible) support subassemblies 54 and 56 about the user's upper 50 and lower 52 arm limb portions, and then fastening the overlapping portions of the respective straps 66 and 68 across the opposite edges 70 and 72 of the rigid backing layers 62 and 74, the clamps 78 and 80 are tightened to draw down together the elbow members 74 and 76. Consistent with the description of FIGS. 1-3, the support subassemblies 54 and 56 are again shown in a pre-positioned and substantially unfolded state relative to the pre-located and assembled rigid elbow members 74 and 76.

The associated angled ledges 90 and 92 of the rigid backing layers are thus seated in abutting and engaging fashion with the opposing ledges 86 and 88 collectively created by the upper and lower encircling and angularly offset perimeter end profiles created by the assembled members 74 and 76, thus securing each semi-flexible support subassembly to the rigid intermediate assembled support members in such a fashion as to create a unitary splint assembly for an individual's arm. Similar to the variant of FIG. 1, the inwardly facing and sponge-like support grids 58 and 60, associated with the support subassemblies 54 and 56, collectively provide, along with the assembled intermediate joint located rigid supports 74 and 76, a temporary, quickly applied and effective splint for immobilizing a user's arm, this again prior to the individual receiving appropriate medical attention (further including such as re-setting a bone fracture and/or applying a permanent cast).

As previously indicated, each of the temporary splint assemblies 10 (for leg) and 48 (for arm) can be provided in a subset number of different sizes, this including three basic sizes in which the wrap-around support subassemblies and intermediate, interlocking, and joint proximate rigid support members each correspond to small, medium, and large sizes. It is also envisioned, in specified instances where a individual's limb injuries are more localized/less severe, only a single wrap around subassembly can be used in combination with the intermediate and rigid joint supporting members, and while still providing a requisite degree immobilizing support.

It is also envisioned that applications of the splint assembly can, beyond operating as a temporary assembly administered by emergency medical technicians, also be reconfigured to function as a long-term and enduring cast configuration. This can also include incorporating a hardenable chemical component into each of the foam-shaped and, initially, flexible grid layers, and such as which can be activated by the introduction of water (or application of frictional engaging contact such as for rupturing a foil or other moisture retaining seal associated with the wraparound layers) following wrapping installation of the support subassembly in the manner described. As previously described, the variously sized splint subassemblies can again being carried by first response (e.g. EMS or paramedic) personnel, and which are quickly and effortlessly applied to secure and adequately immobilize an individual's limb until such time as appropriate medical care can be applied.

Having described my invention, other and additional preferred embodiments will become apparent to those skilled in the art to which it pertains, and without deviating from the scope of the appended claims:

I claim:

1. A splint assembly for use with an individual's limb, comprising;
   a pair of arcuate shaped and rigid assembleable members configured to be positioned in surrounding fashion about an intermediate joint associated with the limb and, upon assembly to immobilize the joint, said assembleable members further defining upper and lower stepped perimeter edges which form edge proximate seating channels;
   at least one wrap around support subassembly exhibiting a grid or web shaped foam template supported by a hardened plastic backing, said support subassembly including an edge extending portion which aligns with a selected one of said seating channels concurrent with securing about a location of the individual's limb contiguous to the joint; and
   a plurality of straps extending from at least one edge of said wrap around subassembly and, upon applying said subassembly to the limb, inter-engaging an opposite edge to maintain in position said subassembly.

2. The splint assembly as described in claim 1, said support subassembly further comprising upper and lower wraparound support subassemblies securing to said opposite edge extending portions associated with said assembleable rigid members.

3. The splint assembly as described in claim 1, said assembleable members comprising a pair of generally semi-cylindrical shaped members corresponding to a knee joint.

4. The splint assembly as described in claim 1, said assembleable members further comprising a pair of elbow shaped members.

5. The splint assembly as described in claim 1, said rigid assembleable members each further constructed of a durable material including at least a lightweight metal or a rigid and impact resistant plastic/composite polymer composition.

6. The splint assembly as described in claim 1, each of said rigid assembleable members further comprising one or more interiorly defined apertures in order to provide a desired degree of ventilation to the individuals joint.

7. The splint assembly as described in claim 4, further comprising at least one clamp for securing and drawing together said elbow shaped members.

8. An immobilizing elbow splint assembly for use with an individual's arm, comprising;
   a pair of arcuate shaped and rigid assembleable members configured to be positioned in surrounding fashion about an elbow joint associated with the individual's arm and, upon assembly to immobilize the joint, said assembleable members further defining upper and lower stepped perimeter edges which form edge proximate seating channels;
   a pair of upper and lower wrap around support subassemblies, each exhibiting a grid or web shaped foam template supported by a hardened plastic backing, said support subassemblies each further including an edge extending portion which aligns with a selected one of said seating channels concurrent with securing about upper and lower arm locations contiguous to the joint; and
   a plurality of straps extending from at least one edge of said wrap around subassembly and, upon applying said subassembly to the limb, inter-engaging an opposite edge to maintain in position said subassembly.

9. The splint assembly as described in claim 8, further comprising at least one clamp for securing and drawing together said elbow shaped members.

10. An immobilizing knee splint assembly for use with an individual's leg, comprising;
    a pair of arcuate shaped and rigid assembleable members configured to be positioned in surrounding fashion about a knee joint associated with the individual's leg and, upon assembly to immobilize the joint, said assembleable members further defining upper and lower stepped perimeter edges which form edge proximate seating channels;
    a pair of upper and lower wrap around support subassemblies, each exhibiting a grid or web shaped foam template supported by a hardened plastic backing, said support subassemblies each further including an edge extending portion which aligns with a selected one of said seating channels concurrent with securing about upper and lower leg locations contiguous to the joint; and
    a plurality of straps extending from at least one edge of said wrap around subassembly and, upon applying said subassembly to the limb, inter-engaging an opposite edge to maintain in position said subassembly.

* * * * *